United States Patent [19]
Vandegriff et al.

[11] Patent Number: 5,226,414
[45] Date of Patent: Jul. 13, 1993

[54] IMPLANTABLE CARDIAC PACEMAKER WITH EXTENDED ATRIAL SENSING

[75] Inventors: Joseph W. Vandegriff, Freeport; Drury L. Woodson, Pearland, both of Tex.

[73] Assignee: Intermedics, Inc., Angleton, Tex.

[21] Appl. No.: 735,072

[22] Filed: Jul. 24, 1991

[51] Int. Cl.⁵ .......................................... A61N 1/368
[52] U.S. Cl. ........................................... 128/419 PG
[58] Field of Search ................................. 128/419 PG

[56]    References Cited
    U.S. PATENT DOCUMENTS

| | | | |
|---|---|---|---|
| 4,365,639 | 12/1982 | Goldryer | 128/419 |
| 4,390,022 | 6/1983 | Calfee et al. | 128/419 |
| 4,404,972 | 9/1983 | Gordon et al. | 128/419 |
| 4,539,992 | 9/1985 | Calfee et al. | 128/419 |
| 4,624,260 | 11/1986 | Baker | 128/419 |
| 4,856,524 | 8/1989 | Baker | 128/419 |
| 4,903,699 | 2/1990 | Baker et al. | 128/419 |
| 4,926,863 | 5/1990 | Alt | 128/419 |
| 4,967,746 | 11/1990 | Vandegriff | 128/419 |

*Primary Examiner*—Kyle L. Howell
*Assistant Examiner*—Kennedy J. Schaetzle
*Attorney, Agent, or Firm*—John R. Merkling

[57] ABSTRACT

A pacemaker with a variable, asynchronous minimum heart rate and a second variable, synchronous heart rate. The second, variable heart rate has an absolute minimum, lower than the asynchronous minimum heart rate, which is preselected by the attending physician. The minimum heart rates can vary, conditioned upon sensed physiologic need. The cardiac pacemaker attempts to reestablish synchrony in every cycle, even if the intrinsic or natural atrial heart rate is below the asynchronous minimum heart rate in that cycle and can maintain cardiac synchrony at lower rates, thereby increasing cardiac efficiency and minimizing strain on the heart.

7 Claims, 4 Drawing Sheets

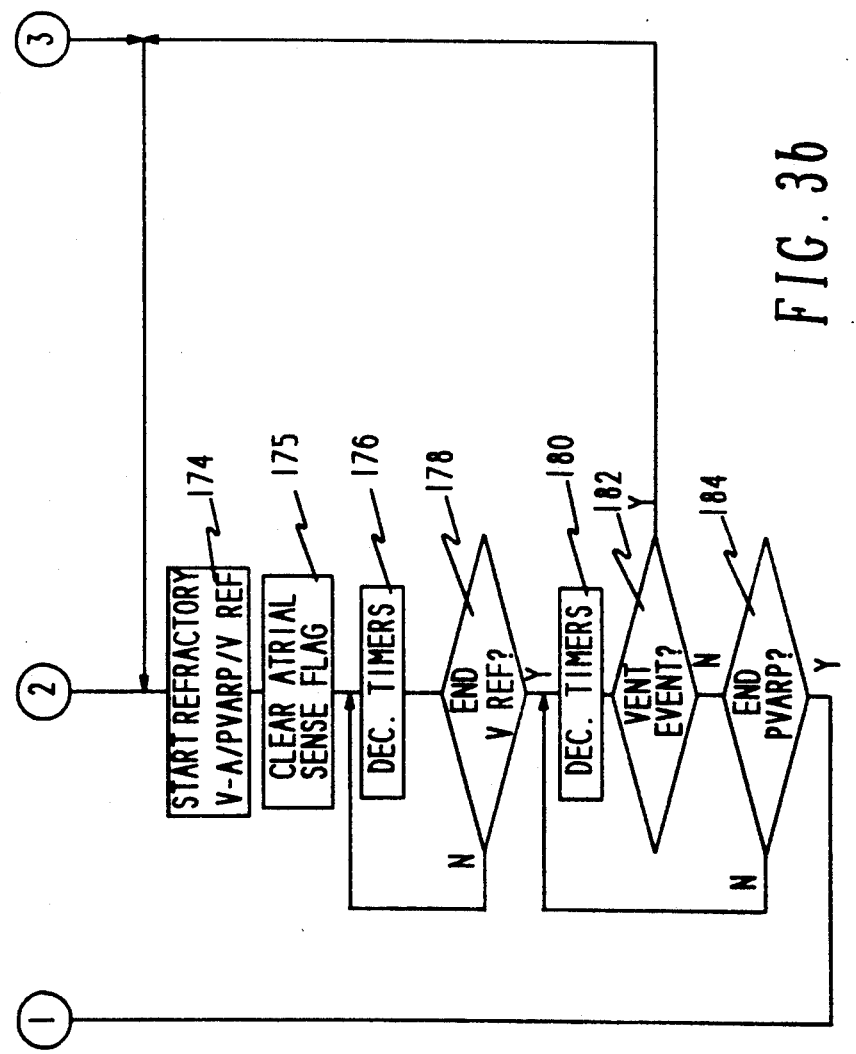

IMPLANTABLE CARDIAC PACEMAKER WITH EXTENDED ATRIAL SENSING

FIELD OF OUR INVENTION

Our invention relates to pacemakers which monitor the operation of the heart and stimulate heart tissue as required to maintain the proper operation of the heart. More particularly, our invention relates to a microprocessor controlled dual chamber pacemaker operating in VDD mode which extends atrial sensing beyond a first predetermined V-A delay to maintain atrial-ventricular synchrony.

BACKGROUND OF THE INVENTION

It has long been known that the heart muscle provides its pumping function in response to electrical events which occur in the atrium and ventricle of the heart. Conductive tissue connects the atrium and the ventricle and provides a path for electrical signals between the two areas. In a normal heart, a natural atrial event spontaneously occurs in the atrium and a corresponding ventricular event occurs later in the ventricle after a time interval typically called the A-V interval. After the ventricular event a new atrial event occurs in the atrium to trigger a succeeding ventricular event. The synchronized electrical events occurring naturally in the atrium and ventricle cause the heart muscle to rhythmically expand and contract and thereby pump blood throughout the body.

In a diseased heart, atrial and ventricular events may not naturally occur in the required synchronized manner and the pumping action of the heart is therefore irregular and ineffective to provide the required circulation of blood within the body. The required synchronized activity of such diseased hearts can be maintained by a pacemaker which applies synchronized stimulating pulses to either the atrium or the ventricle or both.

In the early stages of pacemaker development, pacemakers were employed to asynchronously stimulate the ventricle of the heart without regard to natural electrical activity occurring in either the atrium or the ventricle. Although this approach had the advantage of simplicity, there was considerable risk because paced ventricular events could interact with natural ventricular events to cause a dangerous arrhythmia.

As the art of pacing advanced, pacemakers were provided with circuitry which sensed the occurrence of natural ventricular and atrial activity and paced the heart in either the atrium or ventricle only when required to maintain proper operation of the heart. A dual chamber pacemaker can operate in what is known as DDD mode, wherein electrical events are sensed in the atrium and in the ventricle and the atrium and ventricle are paced accordingly. Pacemakers may also be operated in VDD mode to sense electrical events in the atrium and ventricle but pace only in the ventricle. Other pacemaker modes of operation are employed to sense or pace in either the atrium or the ventricle, as required for the particular needs of a patient.

The effectiveness of the heart as a pump is dependent both on the heart rate and on coordination between the upper and lower chambers of the heart or synchrony between the atrium and the ventricle. When the atrium and the ventricle are coordinated, the heart is relatively more efficient and, therefore, more effective as a pump. If the two chambers are only marginally coordinated, a higher minimum heart rate for the ventricle may be necessary in order to maintain a desired flow. If the two chambers are coordinated, on the other hand, a somewhat lower minimum heart rate can be tolerated.

Prior art VDD pacemakers have not responded adequately to a situation wherein the heart rate is slow but can be synchronized. In general, minimum ventricular heart rates have been set, for example, at a rate of 60 beats per minute. Whether or not synchrony between the atrium and the ventricle was maintained, if the heart rate in the ventricle should fall below the predetermined minimum, the pacemaker would stimulate the heart at the predetermined rate. This could result in a loss of synchrony and a corresponding loss in cardiac efficiency. It is an object of our invention, therefore, to provide a VDD cardiac pacemaker with extended atrial sensing and VDD hysteresis to accommodate synchronous pacing at lower cardiac rates.

It also an object of our invention to provide a VDD pacemaker which provided two minimum rates: a first minimum rate in the absence of synchrony and a second minimum rate, lower than the first minimum, which can be maintained if synchrony is achieved.

For a cardiac pacemaker provided with two minimum rates, as suggested above, it is desirable for the pacemaker to maintain synchrony whenever possible. If the pacemaker, maintaining synchrony, passed the first minimum rate to the absolute second rate, synchrony would be lost. When synchrony was lost, adequate blood flow would only be maintained at the first, relatively higher minimum rate. The pacemaker might jump from the second, lower minimum rate to the first, higher minimum rate. If synchrony can be reestablished within a few cardiac cycles, however, the pacemaker should be able to pace below the first minimum rate. It is an important object of our invention, therefore, to provide a cardiac pacemaker which attempts to provide the capacity to reestablish synchrony in each cardiac cycle. It is also an object of our invention to reestablish synchrony at rates below the first, asynchronous minimum rate, under appropriate circumstances.

Synchrony is important not only at low cardiac rates, but also at high cardiac rates. In rate responsive VDD pacemakers, pacing the ventricle in response to the atrium allows the pacemaker to respond in a physiologic manner. It is possible, however, for the natural pacemaker of the atrium to malfunction at high rates. If this situation occurs, the atrial heart rate may slow even though there is a continuing physiologic need for increased cardiac output and elevated heart rate. Tracking the atrium in such a situation can result in an inappropriate reduction in the ventricular rate. This undesirable situation can be avoided by providing that the minimum asynchronous heart rate be adjustable and dependent upon a sensor correlated to physiologic needs. Such a sensor might be an accelerometer, a thermistor, or an oxygen or pH sensor, as examples. Consequently, an important object of our invention is to provide a VDD pacemaker with an adaptable asynchronous minimum heart rate.

SUMMARY OF OUR INVENTION

We have invented a VDD pacemaker with a variable, asynchronous minimum heart rate and a second variable, synchronous heart rate. The second, variable heart rate has an absolute minimum, lower than the asynchronous minimum heart rate, which is preselected by the attending physician. The minimum heart rates can vary, conditioned upon sensed physiologic need.

We have also provided a cardiac pacemaker which attempts to reestablish synchrony in every cycle, even if the intrinsic or natural atrial heart rate is below the asynchronous minimum heart rate in that cycle. The cardiac pacemaker, according to our invention, can maintain cardiac synchrony at lower rates, thereby increasing cardiac efficiency and minimizing strain on the heart.

These and other features and objects of our invention will be apparent to those skilled in the art from the detailed description and accompanying drawings.

DESCRIPTION OF THE DRAWINGS

FIG. 3 shows the relationship between FIG. 3a and FIG. 3b.

FIG. 3a and FIG. 3b comprise a flow chart for extended atrial sensing and VDD hysteresis according to our invention.

DETAILED DESCRIPTION OF OUR PREFERRED EMBODIMENT

Figure 1:
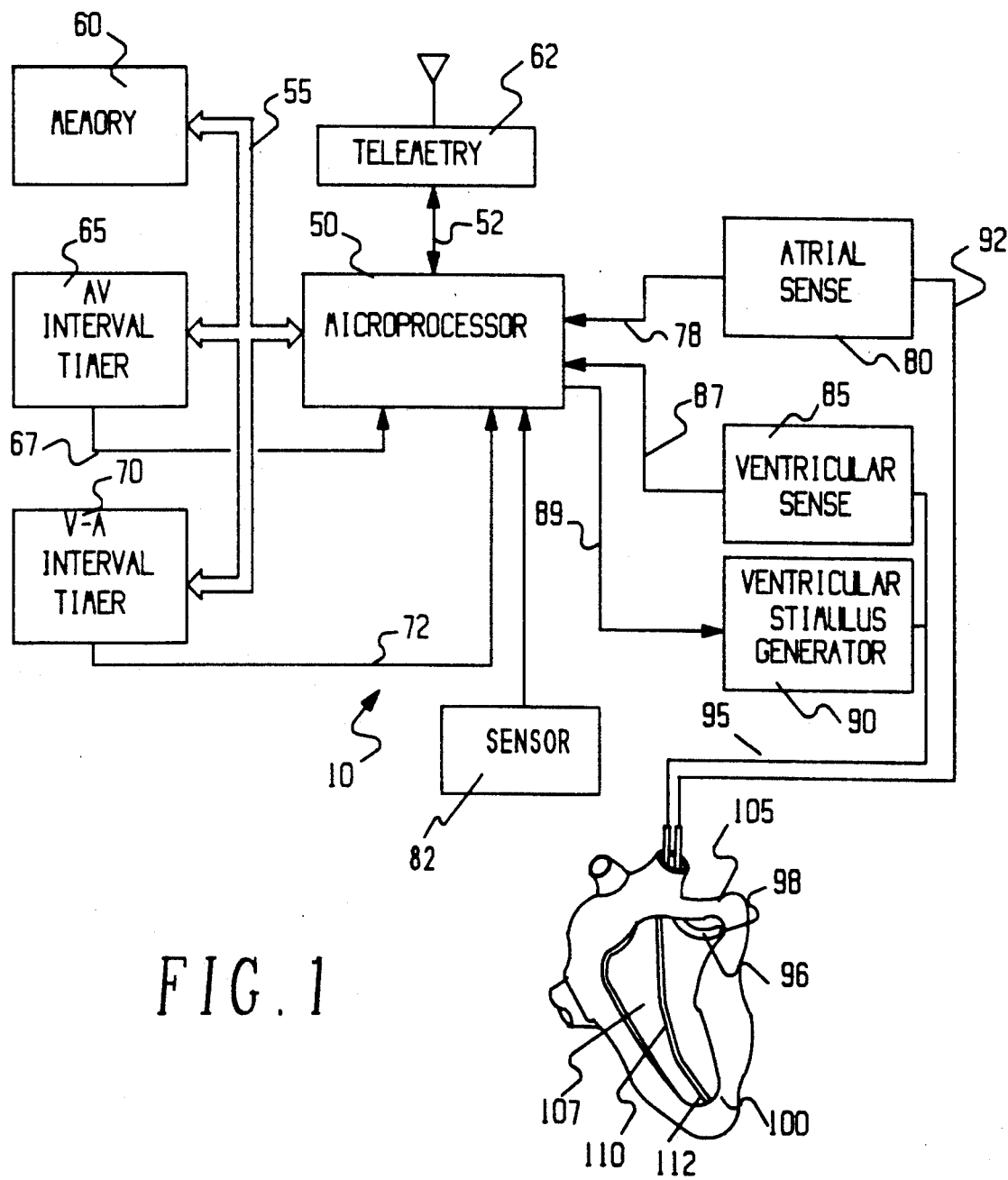
FIG. 1 is a block diagram of a pacemaker suitable for implementation of the present invention.

FIG. 1 is a block diagram illustrating a rate adaptive pacemaker 10 according to our invention. A microprocessor 50 preferably provides pacemaker control and computational facilities. It will be appreciated that other forms of circuitry, such as analog or discrete digital circuitry, can be used in place of microprocessor 50. However, a microprocessor is preferred for its miniature size and its flexibility, both of which are of critical importance in the implantable systems in which it is envisioned the invention will find use. A particularly energy efficient microprocessor which is designed specifically for use in pacemakers is fully described in Gordon et al., U.S. Pat. No. 4,404,972, which is assigned to the assignee of this application. The disclosure thereof is incorporated herein by reference.

The microprocessor 50 has input/output ports connected in a conventional manner via bidirectional bus 55 to memory 60, an A-V interval timer 65, and a V-A interval timer 70. In addition, the A-V interval timer 65 and V-A interval timer 70 each has an output connected individually to a corresponding input port of the microprocessor 50 by lines 67 and 72, respectively.

Memory 60 preferably includes both ROM and RAM. The microprocessor 50 may also contain additional ROM and RAM as described in Gordon et al. U.S. Pat. No. 4,404,972. The pacemaker operating routine is stored in ROM. The RAM stores various programmable parameters and variables used in conjunction with the pacemaker operation.

The A-V and V-A interval timers 65 and 70 may be external to the microprocessor 50, as illustrated, or internal thereto, as described in Gordon et al. U.S. Pat. No. 4,404,972. The timers 65 and 70 are conventional up or down counters of the type that are initially loaded with a count value and count up to or down from the value and output a roll-over bit upon completing the programmed count. The initial count value is loaded into timer 65 and 70 on bus 55 and the respective roll-over bits are output to the microprocessor 50 on lines 67 and 72. The initial count value has a predetermined minimum, either as initially set default by the manufacturer of the pacemaker or as programmed by a physician. The count value set by the microprocessor will vary during use, however, in response to data received by the microprocessor from a sensor 82. The sensor 82 detects a parameter correlated to physiologic need. The sensor may be, for example, an accelerometer to detect motion of a particular type which has shown a correlation to exercise. The sensor may also be another type of physiologic sensor, such as a thermistor to detect central venous or other body temperature, an oxygen content sensor, an impedance sensor, a respiratory sensor or a pH sensor, to name some of the possibilities. We have preferred an accelerometer for its simplicity and have particularly used algorithms such as that described by Alt in U.S. Pat. No. 4,926,863. In response to data from the sensor 82, the microprocessor adjusts the length of the V-A and A-V intervals, shortening the intervals as exercise commences, and lengthening the intervals after exercise until the preselected minimum rates are reached. There are, therefore, dynamic minimum rates dependent upon the sensed need of the user.

The microprocessor 50 preferably also has an input-/output port connected to a telemetry interface 62 by line 52. The implanted pacemaker is thus able to receive pacing and rate control parameters from an external programmer and send data to an external receiver if desired. Many suitable telemetry systems are known to those skilled in the art. One such system and encoding arrangement is described in Calfee et al. U.S. Pat. No. 4,539,992 which is also assigned to the assignee of our invention. That description is incorporated herein by reference.

Microprocessor output ports are connected to an input of a ventricle stimulus pulse generator 90 by control line 89. The microprocessor 50 transmits pulse parameter data, such as pulse amplitude and width, as well as enable/disable and pulse initiation codes, to the generator 90 on the control line 89.

The microprocessor 50 also has input ports connected to outputs of an atrial sense amplifier 80 and a ventricular sense amplifier 85 by lines 78 and 87 respectively. The atrial and ventricular sense amplifiers 80, 85 detect occurrences of P-waves and R-waves respectively. The atrial sense amplifier 80 outputs a signal on line 78 to the microprocessor 50 when it detects a P-wave. This signal is latched to the microprocessor 50 input port by a conventional latch (not shown). The ventricle sense amplifier 85 outputs a signal on line 87 to the microprocessor 50 when it detects a R-wave. This signal is also latched to the microprocessor 50 input port by a conventional latch (not shown).

The input of the atrial sense amplifier 80 is connected to a first conductor 92, which is inserted in a first conventional lead 96. Lead 96 is inserted into the heart 100 intravenously or in any other suitable manner. The lead 96 has an electrically conductive sensing tip 98 at its distal end which is electrically connected to the conductor 92. The sensing tip 98 is lodged in the right atrium 105.

The input of the ventricular sense amplifier 85 and the output of the ventricular stimulus pulse generator 90 are connected to a second conductor 95. The second conductor 95 is inserted in a second conventional lead 110 which is inserted intravenously or otherwise in the right ventricle 107 of the heart 100. The second lead 110 has an electrically conductive pacing/sensing tip 112 at its distal end. The pacing/sensing tip 112 is electrically connected to the conductor 95. The pacing/sensing tip 112 is preferably lodged in the apex of the right ventricle.

The conductor 95 conducts stimulus pulses generated by the ventricular stimulus pulse generator to the pacing/sensing tip 112. The pacing/sensing tips 98 and 112 and corresponding conductors 92 and 95 also conduct sensed cardiac electrical signals in the right atrial appendage and right ventricle to the atrial and ventricular amplifiers 80 and 85 respectively.

The two leads, 96 and 110, may, of course, be replaced by a single lead, such as the lead described in U.S. Pat. No. 4,365,639 to Goldryer. We prefer another single pass lead made by Cardiac Control Systems, for which a patent application is pending in the name of Robert R. Brownlee.

The sense amplifiers 80, 85 enhance the electrical signals. In the preferred embodiments of our invention, the amplifiers 80, 85 have an automatic gain control feature, as described in U.S. Pat. No. 4,903,699 for an "Implantable Cardiac Stimulator with Automatic Gain Control" by Baker, Haluska and one of us (Vandegriff). That patent is assigned to the same assignee as our present invention, and the disclosure thereof is incorporated herein by reference.

Figure 2:
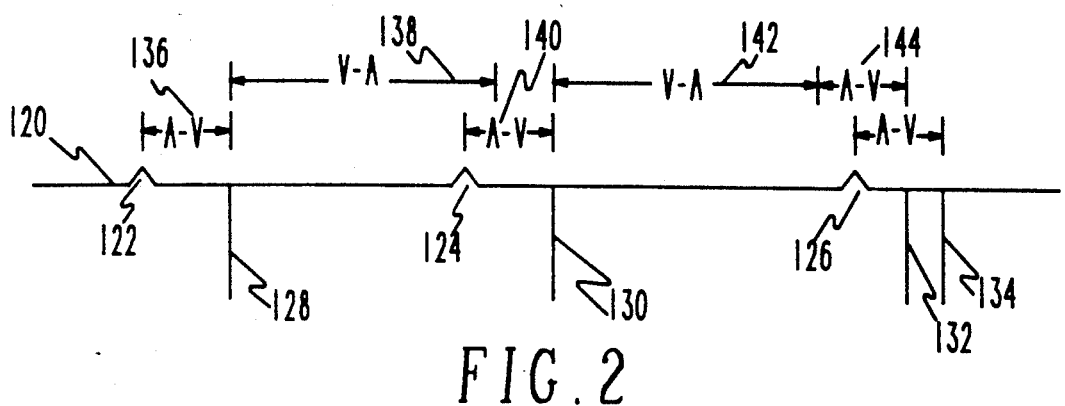
FIG. 2 is a graph showing relative interaction of a paced heart and the pacemaker of FIG. 1.

The output of the pacemaker 10 can be explained with reference to FIG. 2, which is a timing diagram or graph. In FIG. 2, a graphical representation of a cardiac electrogram 120 is shown. Periodic P-waves 122, 124 and 126 are also represented. The P-waves are naturally occurring events in the atrium of the patient's heart. Associated with the P-waves are stimulating pulses 128, 130, 132 and 134. The stimulating pulses would initiate a QRS complex in the ventricle of the heart. For clarity, these well-known waveforms have been omitted from the graph of FIG. 2. In a VDD pacemaker, detection of a P-wave 122 would initiate an A-V delay period 136. After the expiration of the A-V delay period 136 the ventricle would be simulated at 128. This will conventionally initiate the beginning of V-A delay 138. If a second P-wave 124 is detected during the V-A delay 138, a second A-V delay 140 is initiated. The atrium of the heart is then beating at a rate greater than a preselected minimum and the ventricle can be paced in synchrony with the atrium. At the end of the second A-V delay 140 the ventricle is again paced 130.

A different situation occurs in the conventional VDD pacemaker if the P-wave 126 is not detected within a second V-A delay period 142. In this situation, an A-V delay period 144 will be commenced immediately after the V-A delay period and at the end of the A-V delay the ventricle will be paced by stimulus 132. In the VDD pacemaker of our invention, however, the late P-wave 126 is not ignored. The A-V delay is commenced as in A-V delay 144. Upon the occurrence of the P-wave 136, however, the A-V delay is restarted so that a later, but synchronous stimulus 134 can now be administered to the ventricle of the heart. If no P-wave is detected during the A-V interval 144, the ventricle is paced at 132.

There is, therefore, a first, asynchronous minimum ventricular heart rate limited by the sum of the V-A and A-V delay periods and a second, lower synchronous minimum heart rate bounded by the length of one V-A delay period and two A-V delay periods. As explained above, the V-A and A-V delay periods can be dynamically adjusted, in response to a detected physiologic need, to avoid a sudden decline in heart rate upon loss of synchrony.

Figure 3A:
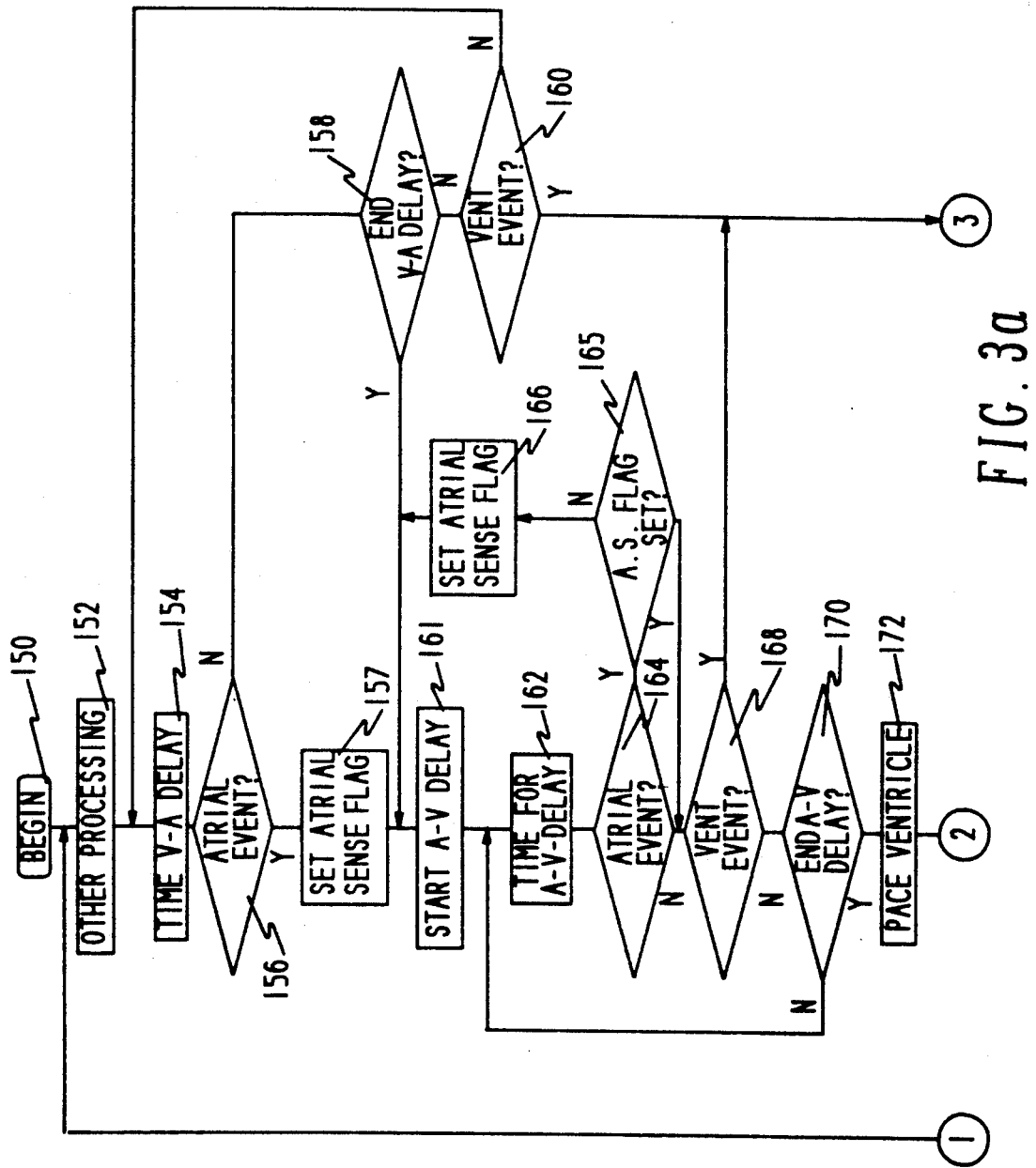

A software routine implementing our invention will be described with reference to FIG. 3a and FIG. 3b. In our preferred embodiment, we utilize a method of turning off unused portions of the cardiac pacemaker to conserve energy, an important consideration in an implantable device. This technique is described in detail in U.S. Pat. No. 4,390,022 to Calfee and Minor for an "Implantable Device with Microprocessor Control", a patent assigned to the same assignee as our present invention. The process of turning off particular sections of the microprocessor or other circuitry is called "sleep"; turning on a portion of the circuitry is called "wake up". Detected events initiate the wake up procedure and are referred to as "wake up events". Further information on this technique is available in the mentioned patent.

As is common in implanted pacemakers, the processing in an implanted microprocessor, such as microprocessor 50, runs in a loop or cycle. The programs to implement our invention would be part of such an overall cycle. When microprocessing in the microprocessor 50 begins 150 such conventional processes would also be implemented. They are indicated in FIG. 3 as other processing 152 and will not be furthered described herein. Commencing the implementation of our invention, the microprocessor 50 would initiate a V-A delay timer 154. This is a count down timer represented at 70 in FIG. 1. In addition, pending a ventricle sense, atrial sense, or end of V-A delay, portions of the circuitry would be put to sleep in the manner described above. Sensing for wake up events would be initiated. The microprocessor would test for the sense of an atrial event 156. If no atrial event as sensed, the microprocessor 50 tests for the end of the V-A delay 158. If the V-A delay has not ended, the microprocessor tests for a sensed ventricular event 160. If no ventricular event has been detected, program control returns to the time V-A delay step 154 so that the counter can be decremented. This loop is repeated until one of the three conditions 156, 158 and 160 is met. If either an atrial event is sensed 156 or the end of the V-A delay has occurred 158, processing will commence which will terminate in a pace of the ventricle, as will be more fully described below. If a spontaneous ventricular contraction is detected 160, programming skips past a pace of the ventricle 172.

If an atrial event is sensed, an atrial sense flag is set 157 to indicate detection of an atrial contraction. If either an atrial event is sensed 156 or the end of the A-V delay has occurred 158, the A-V delay period timer is started 161. The timer is decremented to time the A-V delay 162. The pacemaker 10 continues to test for sensing of an atrial event 164. If an atrial event is detected before the expiration of the A-V delay, the microprocessor tests an atrial sense flag 165. The A-V delay should preferably be reset only once. Otherwise, atrial fibrillation could indefinitely postpone pacing in the ventricle. If the flag had not been set since a ventricular pulse, the flag is set 166 and the A-V delay period is started 166 again. This maintains synchrony between the atrium and the ventricle at a lower rate than might be otherwise be expected.

If the flag has been set or if no atrial event is detected during a particular loop, the microprocessor 50 tests for sense of a ventricular event 168. As is known, if a ventricular contraction spontaneously occurs in response to the contraction of the atrium, no pace in the ventricle is necessary and control skips past the ventricle pace step 172. If no ventricular event is detected, the microprocessor 50 tests for the end of the A-V delay period 170. If the A-V delay period has not ended, the A-V delay timer is again decremented and the loop as heretofore described is reiterated. If the A-V delay period has ended, the ventricle is paced 172.

The heart has now experienced either a spontaneous (or natural) ventricular contraction or a paced ventricular contraction. The microprocessor 50 initiates a refractory subroutine 174. In the refractory subroutine 174 certain conventional features are implemented. A V-A delay period, a post-ventricular atrial refractory period and a ventricular refractory are started. The post-ventricular atrial period or "PVARP" and the ventricular refractory period are periods of time during which the sensors of the pacemaker in the atrium or ventricle respectively are not responsive to electrical signals. As is known, these periods are chosen to inhibit detection of spurious signals which may result in pacemaker mediated tachycardia, a condition of high heart rate because of inappropriate interaction between the pacemaker and the heart. In addition, adaptive A-V and V-A delay periods may be calculated at this stage.

With the V-A delay, PVARP and refractory periods commenced, the microprocessor 50 also clears the atrial sense flag 175 and decrements timers 176. It then tests for the end of the ventricular refractory period. If the refractory period has not ended, the microprocessor will return to decrement the various periods 176. If the ventricular refractory period has ended, the microprocessor 50 will continue to decrement the PVARP and the V-A delay 180. It will test for a sense in the ventricle 182 and if a ventricular event is detected, it will return control to step 174. It will also test for the end of the PVARP 184 and continue to decrement the PVARP timer until the end of the PVARP. After the end of the post-ventricular atrial refractory period, control will return to other processing 152.

Figure 4:
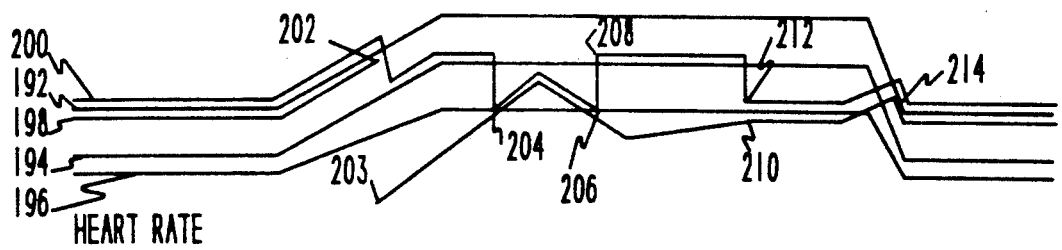
FIG. 4 is a graph of an example of a response of a pacemaker according to our invention.

The operation of our invention over time can be understood with reference to FIG. 4, which illustrates in graphical form an example of a pacemaker response to changing conditions. FIG. 4 shows an exercise level 190 which represents a physiologic need of a patient over time. The exercise level 190 begins at a resting level, rises to a plateau, continues for a period of time, declines, and finally returns to the resting level. FIG. 4 also shows a set of heart rates corresponding to this exercise situation. Line 192 represents an optimum heart rate, the heart rate at which a healthy heart would beat in response to the exercise of line 190. This rate corresponds quite well to the demands placed on the heart and body of the patient in response to exercise. In the pacemaker patient, there is an asychronous minimum heart rate 194. The resting rate of this asynchronous heart rate is set by the physician or is a default parameter when the pacemaker is implanted. In FIG. 4, the asynchronous rate 194 is shown initially somewhat below the optimum rate. In a rate adaptive pacemaker with a physiologic sensor, such as the pacemaker described herein, the asynchronous minimum rate changes in response to exercise or other physiologic need as detected by the sensor 82. This phenomenon can be seen in the rise, plateau and decline of line 194. In general, this adjustment takes place by adjusting A-V and V-A intervals, as described above.

In a pacemaker according to our invention there is also a synchronous minimum rate 196. The synchronous minimum rate 196 is below the asynchronous rate and is a function thereof. Since rates are shown in FIG. 4, not periods, the relationship between the asynchronous rate 194 and the synchronous rate 196 is not linear and change in the two rates does not result in a parallel graph. Also shown in FIG. 4 are the actual atrial rate 198 and the paced ventricular rate 200. For this example we are assuming that the ventricle is always paced. The atrial rate 198 and the ventricular rate 200 are slightly displaced away from the optimum line for ease in reading the graph. The atrial rate 198 is displaced slightly downwardly and the ventricular rate is displaced slightly upwardly. Otherwise, in the initial portion of the graph, both the atrial rate 198 and the ventricular rate 200 would fall on the optimum rate 192.

In this example, the atrial rate 198 follows the optimum rate 192 and begins to increase as exercise increases. The ventricular rate 200 is following the atrial rate. At a point 202 we have assumed that the natural pacemaker of the atrium begins to misfunction and there is a sudden, discontinuous decline in the atrial rate to a second point 203. The sensor 82, however, is still indicating increased physiologic need. The atrial rate has fallen well below either the asynchronous rate 194 or the synchronous minimum rate 196, so the pacemaker would adjust the ventricular rate to the asynchronous minimum 194, as adjusted for exercise or physiologic need. The ventricular rate 200 would track the asynchronous minimum rate until the atrial rate met or exceeded the synchronous minimum rate 196 at point 204. At that time, the ventricular rate would drop to track the atrial rate. This is because synchrony between the atrium and the ventricle would produce increased hemodynamic performance even at the slightly lower rate. The ventricular rate would then track the atrial rate until the atrial rate fell below the synchronous minimum 196 at 206. The ventricular rate would jump up to the asynchronous minimum at 208. If the atrial rate returns to the synchronous minimum at 210, the ventricular rate will again match the atrial rate at point 212. The atrium may also return to the optimum rate at 214 with the ventricular rate following the atrial rate.

From the foregoing it will be apparent that there are two minimum rates, each adjusted for physiologic need. Moreover, the pacemaker of our invention will attempt to reestablish synchrony in every cardiac cycle as between the asynchronous minimum and synchronous minimum rates.

Our invention may be embodied in other specific forms without departing from the spirit or essential characteristics thereof. The present embodiment is therefore considered in all respects to be illustrative and not restrictive, the scope of our invention being indicated by the appended claims rather than by the foregoing description and all changes which come within the meaning and range of equivalency of the claims are therefore intended to be embraced therein.

We claim as our invention:

1. An implantable cardiac pacemaker comprising
means for sensing a spontaneous contraction in an atrium of a heart;
means for sensing a contraction in a ventricle of the heart;
timing means for timing a V-A delay period after a contraction in the ventricle of the heart;
second timing means for timing a first A-V delay period commencing with the first to occur of either a contraction of the atrium or the expiration of said V-A delay period;

means for re-starting said A-V timing means before the expiration of said first A-V delay period to time a second A-V delay period when a contraction is detected in the atrium by said spontaneous contraction detecting means before expiration of said first A-V delay period; and means for stimulating the ventricle of the heart at the end of said A-V delay period in the absence of a sensed contraction in the ventricle during said A-V delay period.

2. The implantable cardiac pacemaker according to claim 1 further comprising
   means for sensing a parameter correlated to physiologic need; and
   means for adjusting said A-V delay period and said V-A delay period in response to said sensed physiologic need.

3. The implantable cardiac pacemaker according to claim 2 wherein the physiologic need sensing means comprise an accelerometer.

4. An implantable cardiac pacemaker comprising
   means for sensing contractions in an atrium of a patient's heart;
   means for stimulating a ventricle of the patient's heart in synchrony with atrial contractions;
   means for limiting output of the stimulating means to a first minimum heart rate at least whenever the rate of atrial contractions is less than a second minimum heart rate, said second minimum heart rate being lower than said first minimum heart rate;
   means for limiting output of the stimulating means to a rate above said second minimum heart rate whenever the stimulating means is able to stimulate the heart in synchrony with contractions in the atrium; and
   means for selecting between the first and second minimum heart rates during each cardiac cycle.

5. The cardiac pacemaker according to claim 4 further comprising
   sensor means for detecting a parameter correlated to physiologic means; and
   means for adjusting the first and second minimum heart rates based on the detected parameter.

6. The cardiac pacemaker according to claim 5 wherein the adjusting means adjusts the said minimum heart rates in each cardiac cycle.

7. The cardiac pacemaker according to claim 6 wherein the sensor means comprise an accelerometer.

* * * * *